United States Patent [19]

DeCote, Jr.

[11] Patent Number: 4,729,376

[45] Date of Patent: Mar. 8, 1988

[54] CARDIAC PACER AND METHOD PROVIDING MEANS FOR PERIODICALLY DETERMINING CAPTURE THRESHOLD AND ADJUSTING PULSE OUTPUT LEVEL ACCORDINGLY

[75] Inventor: Robert DeCote, Jr., Miami Beach, Fla.

[73] Assignee: Cordis Corporation, Miami, Fla.

[21] Appl. No.: 738,606

[22] Filed: May 28, 1985

[51] Int. Cl.$^4$ .............................................. A61N 1/36
[52] U.S. Cl. ............................................ 128/419 PT
[58] Field of Search ....... 128/419 P, 419 PG, 419 PT

[56] References Cited

U.S. PATENT DOCUMENTS

| | | | |
|---|---|---|---|
| 3,433,228 | 3/1969 | Keuer, Jr. ..................... | 128/419 PG |
| 3,683,934 | 8/1972 | Bukoniecki et al. .......... | 128/419 PG |
| 3,757,790 | 9/1973 | Herrmann ..................... | 128/419 PT |
| 3,777,762 | 12/1973 | Nielsen ......................... | 128/419 PT |
| 3,800,801 | 4/1974 | Gaillard ........................ | 128/419 PT |
| 3,920,024 | 11/1975 | Bowers ......................... | 128/419 PG |
| 3,949,758 | 4/1976 | Jirok ............................. | 128/419 PG |
| 4,245,643 | 1/1981 | Benzing, III et al. ........ | 128/419 PT |
| 4,273,132 | 6/1981 | Hartlaub et al. ............. | 128/419 PG |
| 4,290,430 | 9/1981 | Bihn et al. .................... | 128/419 PT |
| 4,337,776 | 7/1982 | Daly et al. .................... | 128/419 PT |

OTHER PUBLICATIONS

A New Electronic System for the Detection of the Stimulated Cardiac Response, J. Mugica, B. Lazarus, D. Delle-Vedove, Y. Lallemand, O. Hubert.

Primary Examiner—William E. Kamm
Attorney, Agent, or Firm—Lockwood, Alex, FitzGibbon & Cummings

[57] ABSTRACT

A low-power cardiac pacer and method includes an automatic capture threshold determination system wherein the minimum pulse energy required to reliably stimulate contractions of a patient's heart is periodically determined. The energy level of pacing pulses generated by the pacer is automatically set in accordance with the determined capture threshold level to reduce battery current drain and thereby extend the pacer's useful life.

12 Claims, 4 Drawing Figures

CARDIAC PACER AND METHOD PROVIDING MEANS FOR PERIODICALLY DETERMINING CAPTURE THRESHOLD AND ADJUSTING PULSE OUTPUT LEVEL ACCORDINGLY

BACKGROUND OF THE INVENTION

The present invention relates generally to cardiac pacers, and pacing methods and more particularly to a battery-powered implantable cardiac pacer and method in which the minimum pacing pulse energy required to reliably stimulate a patient's heart is determined and pacing pulse output level is automatically adjusted in accordance therewith to maximize battery life.

Cardiac pacers are beneficially used in the treatment of a variety of cardiac disorders. The operating requirements placed on a cardiac pacer often vary widely in accordance with both the nature of the particular disorder to be treated, and with the specific needs of an individual patient. It is therefore a common and well known practice to construct pacers such that the various pacer operating parameters can be adjusted over a considerable range. This is particularly advantageous since the economic benefits of large volume production can then be realized without restricting a physician's ability to tailor pacer operation according to a patient's individual needs.

While the ability to control various aspects of pacer operation provides many advantages, the flexibility thus afforded requires that consideration be given to a number of factors in selecting the pacer operating parameters. It is of course vital that the pacing output energy be sufficient to reliably stimulate the heart. Yet, battery current drain should be minimized in order to avoid the need for premature battery replacement surgery. It is also desirable that normally occurring changes in the patient's own physiological parameters will not necessitate physician readjustment of pacer operation.

Previously, pacer output energy level was set by a physician in accordance with a patient's "capture threshold" determined at the time of pacer implantation. This threshold, which represents the minimum pacing energy required to reliably stimulate a patient's heart, provided a useful starting point in selecting the pacer output energy level. However, since capture threshold typically increases over time as scar tissue grows at the interface between the implanted cardiac pacer leads and the myocardium, the usual present procedure is to set the pacer output level to a minimum of three or four times the initially measured capture threshold. While this procedure assures reliable cardiac stimulation, battery current drain is clearly above the theoretical optimum minimum level which would result if the pacer could at all times be operated at, or slightly above, the actual capture threshold existing at any particular moment.

Previously, however, capture threshold could only be measured indirectly through a laborious and time consuming procedure involving several manipulations of pacer level. In one previous external pacer, pacer level could be momentarily reduced by a predetermined constant factor in response to actuation of a push button control on the pacer housing. While this greatly increased the speed with which a physician could determine the post-implantation capture threshold, readjustment of the actual pacing output level nevertheless required the intervention of the physician. Safety dictated that the pacing level be set in the implanted pacer substantially greater than the measured capture threshold in order to assure reliable stimulation in the event the capture threshold increased substantially, before a physician could intervene. Thus, in the absence of a reliable, rapid and automatic capture threshold determination system, which could be directly incorporated into either an implantable or external cardiac pacer, any attempt to operate close to the actual capture threshold created a substantial risk that pacing reliability would be compromised as the lead-myocardium interface aged.

The present invention is directed to a cardiac pacer and method which automatically determines a patient's actual capture threshold and then sets the pacing energy level slightly above the threshold so determined. The pacer further includes a system for monitoring the sufficiency of the generated pacing pulses such that the capture threshold is redetermined, and the pacing level reset, any time it appears that the currently generated pacing pulses are not reliably stimulating the heart. Accordingly, the pacer can be arranged to operate slightly above the actual capture threshold without incurring a loss of pacing reliability. This significantly increases battery life while simultaneously avoiding the need for frequent manual readjustment of pacing pulse level.

In view of the foregoing, it is a general object of the present invention to provide a new and improved cardiac pacer and method of pacing.

It is a further object of the present invention to provide a cardiac pacer and method of pacing which minimizes battery current drain while retaining pacing functional reliability.

It is still a further object of the present invention to provide an improved cardiac pacer which operates slightly above the patient's actual capture threshold.

SUMMARY OF THE INVENTION

The present invention is directed to a cardiac pacer and pacing method for stimulating contractions of a patient's heart. The pacer includes a pulse generator for generating a series of pacing pulse pairs, each of which includes two pacing pulses separated in time by less than the refractory period of the patient's heart. An automatic capture threshold determination system is provided for automatically determining the minimum pacing pulse energy required to reliably stimulate contractions of the patient's heart. The energy of the generated pacing pulse pairs is set in accordance with the capture threshold so determined, such that pacing occurs at an energy level slightly above the patient's measured capture threshold.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
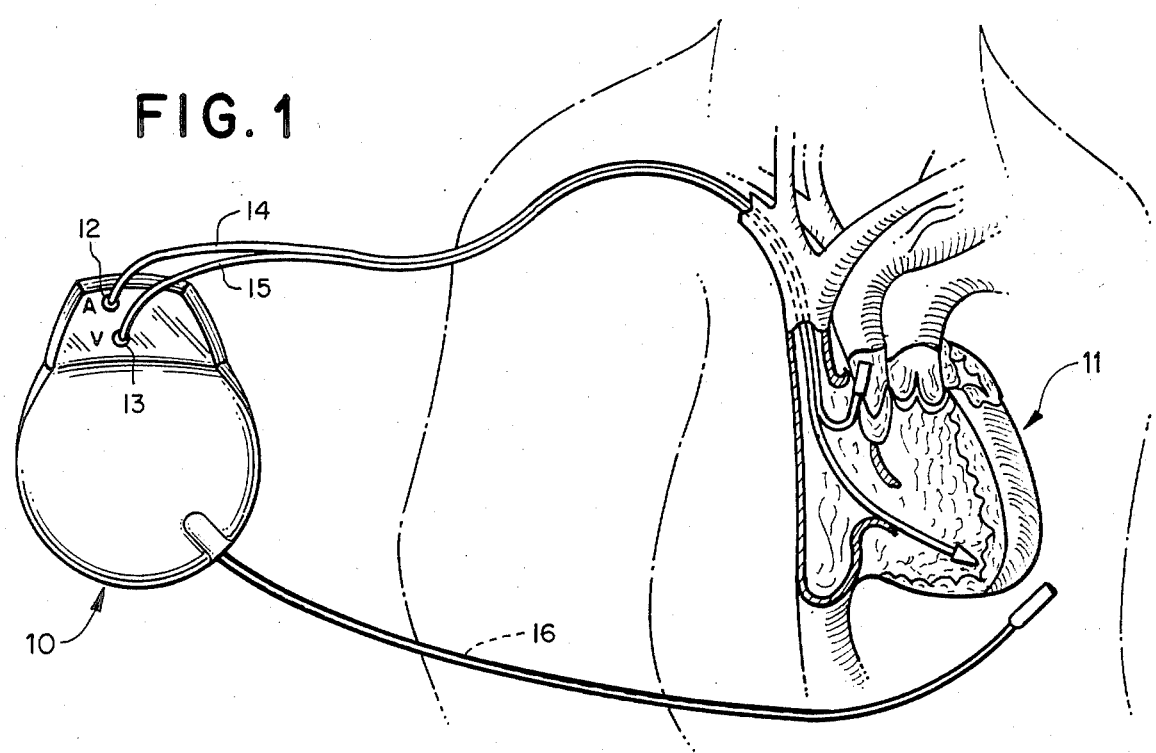
FIG. 1 is a perspective view of an implantable pacer having an automatic capture threshold determination system constructed in accordance with the invention.

Referring to the Figures, and in particular to FIG. 1, a battery operated implantable programmable cardiac pacer 10 constructed in accordance with the invention is shown in conjunction with a patient's heart 11. Pacer 10 develops atrial and ventricular pacing pulses which are made available at respective atrial and ventricular output terminals 12 and 13. Output terminals 12 and 13 are respectively connected to the ends of atrial and ventricular pacing leads 14 and 15 of known (unipolar or bipolar) construction. The distal ends of leads 14 and 15 have been implanted in the atrial and ventricular myocardial tissue in known manner. An additional electrode 16, which may comprise an electrically conductive surface on the pacer housing, provides a reference for the atrial and ventricular unipolar terminals. Pacer 10 is preferably formed as a self-contained and hermetically sealed device such that its operation is unaffected by exposure to body fluids.

Figure 2:
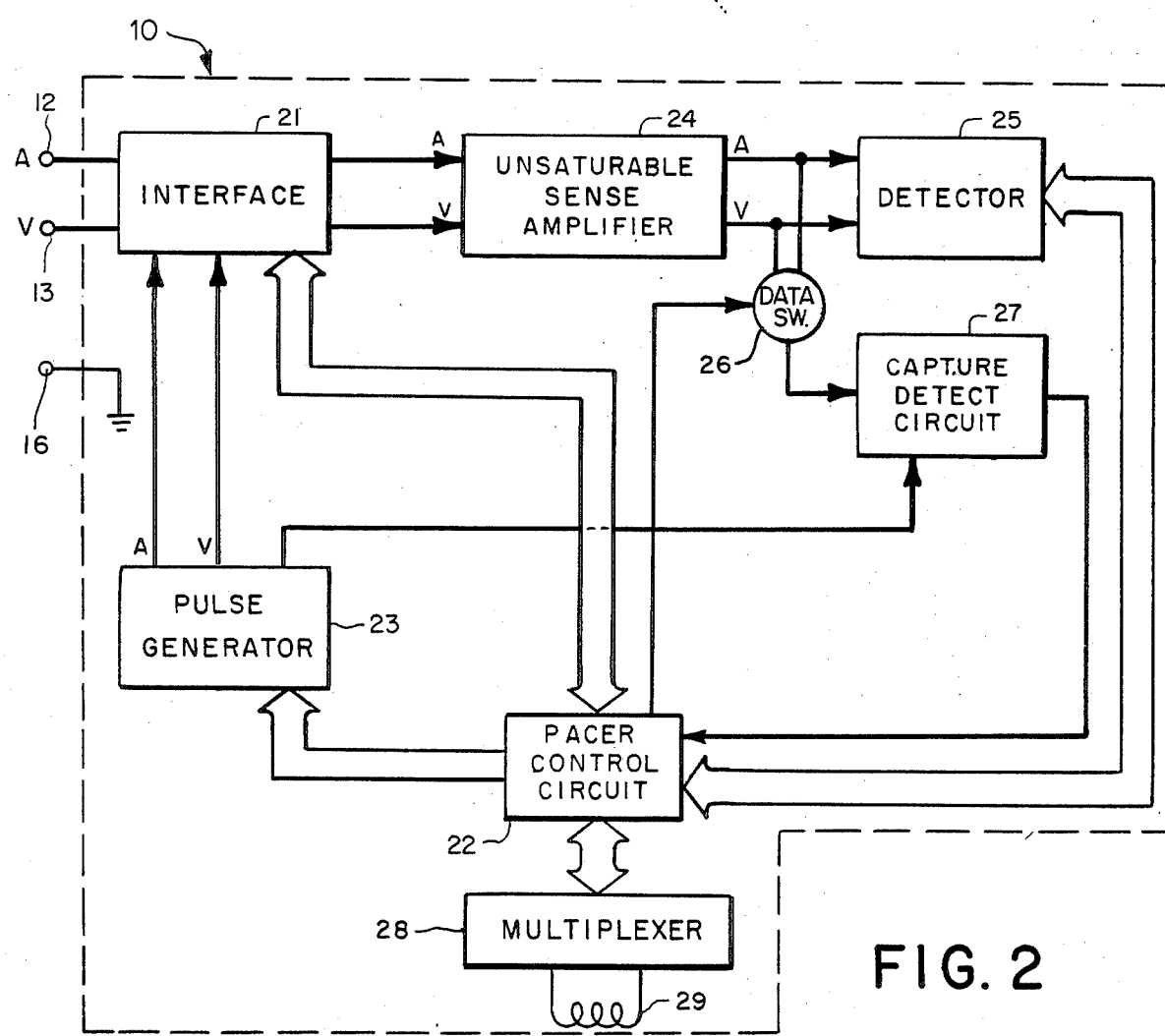
FIG. 2 is a functional block diagram showing the principal elements of the cardiac pacer illustrated in FIG. 1.

Referring to FIG. 2, atrial and ventricular pacer terminals 12 and 13 are individually connected to an interface circuit 21 wherein appropriate electrical connections are established between the pacing leads and the sensing and pacing circuitry of the pacer in accordance with the user-selected operating mode. Interface 21 operates under the control of pacer control circuit 22. A pulse generator 23, also under control of the pacer control circuit 22, generates atrial and ventricular pacing pulses which are applied through interface circuit 21 to the atrial and ventricular terminals 12 and 13

Pacer 10 further includes a two channel unsaturable sense amplifier 24 for amplifying atrial and ventricular cardiac response signals sensed by the atrial and ventricular pacing leads 14 and 15. The unsaturable sense amplifier 24, which is described in the concurrently filed application Ser. No. 738,608 of the present inventor entitled "Unsaturable Sense Amplifier for Pacer System Analyzer", is not driven into saturation by applied pacing pulses and is therefore capable of sensing and amplifying whatever cardiac response signals are developed immediately following each applied pacing pulse. The output of sense amplifier 24 is coupled to a sense threshold detector circuit 25 which, in known manner, detects naturally occurring cardiac contractions and allows the pacer to operate in a well known "demand" mode wherein pacing pulses are generated and applied to the heart only when the naturally occurring heart beat falls below a predetermined rate.

In accordance with one aspect of the invention, the outputs of the unsaturable sense amplifier are synchronously coupled through a two position data switch 26 to a capture detect circuit 27 which operates to detect cardiac contractions induced by sequential atrio-ventricular pacing pulses applied to the heart. Data switch 26 operates under the control of the pacer control circuit 22 such that the atrial and ventricular outputs of sense amplifier 24 are sequentially coupled to capture detect circuit 27. The capture detect circuit 27 operates in conjunction with the pulse generator 23 and provides a capture indicative control signal to pacer control circuit 22 upon each occurrence of an induced cardiac contraction.

Pacer 10 is capable of operation in either a demand mode, wherein pacing pulses are provided only when needed, or in a "free running" mode wherein pacing pulses are continually generated and applied to the heart at predetermined rate. The addition of the capture detect circuit 27 provides, in either operating mode, the ability to automatically determine the patient's capture threshold in each chamber and to automatically adjust the pacing pulse energy level in accordance with the capture thresholds so determined. Thus, the pacing pulse level will change automatically in the event of a change in the capture threshold and will normally not require manual readjustment. User selection of the desired operating mode is provided by means of a multiplexer 28, coupled to pacer control circuit 22, and a pickup element 29. Appropriately coded magnetic or radio frequency control signals are coupled to the pickup element 29 in known manner to provide user selection of the operating mode from a remote external location.

The operation of the capture detect circuit 27, which is described in detail in the present inventor's concurrently filed application Serial No. 738,609, entitled "System and Method for Detecting Evoked Cardiac Contractions" is based on the recognition that if pacing pulses are applied to the heart in pairs, and if the pulse spacing within a pair is less than the refractory period of the heart, then, at most, only one pulse of the pair can induce cardiac capture. It has been experimentally determined that when the myocardium depolarizes, it becomes refractory for at least 150 milliseconds. Accordingly, pacing pulses generated in pairs spaced by a nominal 100 millisecond interval should, when applied to the heart, produce at most one contraction per pulse pair.

The operation of the capture detect circuit 27 is further based on the observation that post-pulse lead recovery artifacts are essentially completely decayed within 50 milliseconds following the end of each pacing pulse. Accordingly, the lead recovery artifact waveforms, produced in response to each pulse of a pulse pair, will be essentially identical in the absence of any induced cardiac response event. Thus, a properly implemented waveform subtraction of the lead recovery curves will yield a near-zero result in the event neither pulse of a pair induces capture. However, if either pulse induces a contraction of the heart, subtraction of the lead recovery curves will produce a detectable waveform difference. Since contractions evoked by both pulses of a pair is an impossibile condition, it follows that an induced cardiac contraction will always result in a non-zero waveform difference.

In order to implement the capture detection function, it is necessary that the pacing control circuit 22 and pacing pulse generator 23 initially function to develop paired pacing pulses for application to the heart. Typically, each pulse pair will consist of two identical pulses spaced by less than the refractory period of the heart, while the interval between pairs is sufficient to provide a repetition frequency between 40 and 120 pulse pairs per minute.

Figure 3:
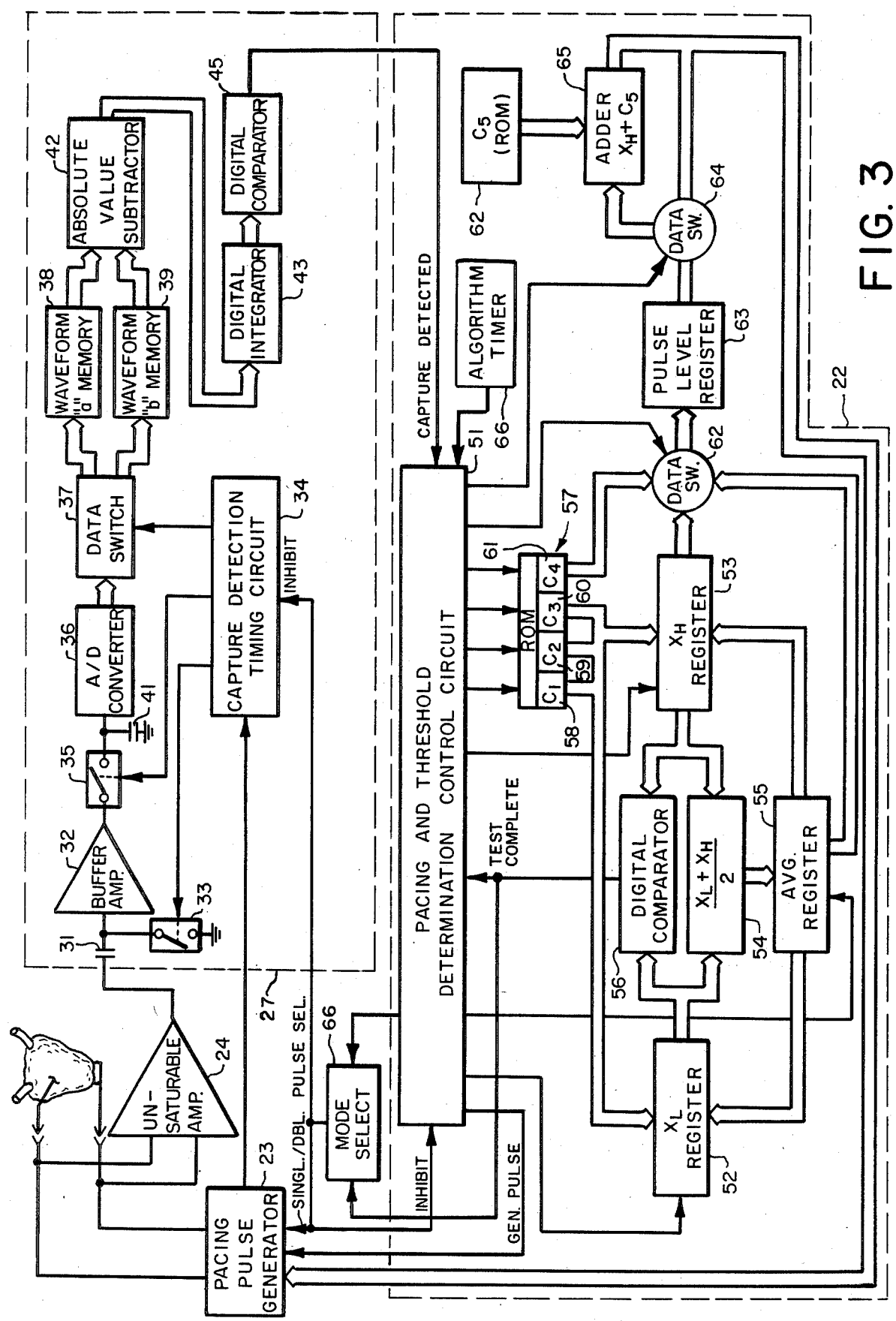
FIG. 3 is a simplified block diagram of the automatic capture threshold determination system incorporated into the cardiac pacer of FIG. 1.

As illustrated in FIG. 3, an output of unsaturable amplifier 24 is coupled to the capture detect circuit 27 as is a control output from pacing pulse generator 23. For simplicity, only one channel is shown. As is further illustrated, the output of amplifier 24 is coupled through a capacitor 31 to the input of a buffer amplifier 32. The input of buffer amplifier 32 is also connected through a voltage controled analog switch 33 to circuit ground. A control voltage for controlling the operation of the analog switch is developed by a capture detection timing circuit 34 which develops a series of additional control voltages for controlling the operation of the capture detection circuit.

The output of buffer amplifier 32 is connected through a second voltage controlled switch 35 to the input of an analog-to-digital converter (ADC) 36, the output of which is coupled through a two-position data switch 37 to either of two digital waveform memories 38 or 39. Control voltages for controlling switches 35 and 37 are also developed by the capture detection timing circuit 34. A capacitor 41 is connected between the input of ADC 36 and circuit ground, and, together with switch 35, forms a sample and hold circuit having a sampling frequency determined by the capture detection timing circuit 34.

Capacitor 31 and analog switch 33 form a gated clamp which operates under the control of the capture detection timing circuit 34. Switch 33 closes when a LOGIC-HIGH gated clamp control signal is developed by the capture detection timing circuit, and opens when the gated clamp control voltage is LOGIC-LOW.

The timing of the gated clamp control signal is such that switch 33 is made to close during a period beginning just before each output pacing pulse and terminating a few milliseconds after the completion of each pulse. The effect is that the heaviest pacer pulse artifacts are thereby squelched. While switch 33 is closed, capacitor 31 will be charged to the output voltage of amplifier 24. Accordingly, immediately after the switch opens, the input to the buffer amplifier 32 will consist of the instantaneous output of the unsaturable amplifier 24 offset by the voltage to which capacitor 31 has been charged at the instant the switch opens. This assures that the initial voltage applied to the input of buffer amplifier 32 will be equal to ground potential, and any subsequent change in the output voltage of unsaturable amplifier 24 will appear as an identical change relative to ground at the input of the buffer amplifier. This function of the gated clamp serves to assure that the full dynamic range of ADC 36 is utilized since no matter what the actual output voltage of sense amplifier 24 is, the input voltage to buffer amplifier 32 will initially be zero volts and will then change from that potential in accordance with subsequent changes in the sense amplifier output voltage.

During the period in which analog switch 33 is open, the output of buffer amplifier 32 is converted to a series of digitally encoded data words by means of switch 35, capacitor 41 and ADC 36. The sampling rate, determined by the capture detection timing circuit 34, is selected so as to provide an accurate digital representation of the output of the buffer amplifier. Thus, each of the lead response waveforms, produced in response to each pulse of a pulse pair, will be converted to a corresponding digital representation.

From ADC 36, the digital waveform representations so developed are coupled through data switch 37 to either of the two waveform memories 38 or 39. Timing circuit 34 controls data switch 37 such that the response waveform produced by the first pulse of a pair is at all times stored in waveform memory 38, while the response signal produced by the second pulse of a pair is at all times stored in waveform memory 39. Thus, following the generation and application of each paired pacing pulse, waveform memories 38 and 39 will contain the gated digitized response signals developed by the first and second pulses respectively of a pulse pair.

Once digitized and stored in waveform memories 38 and 39, the gated response waveforms produced by the first and second pulses of a pulse pair are compared by means of a digital absolute value subtractor 42, which compares the corresponding bytes of the waveforms, to develop a digital signal indicative of the absolute difference therebetween. This absolute difference or "delta" signal is applied to the input of a digital integrator 43 which integrates "delta" over a predetermined time interval. The integrated "delta" signal is coupled to a digital comparator 45. When the integrated delta value exceeds the comparator threshold value, a "CAPTURE DETECTED" logic signal is developed and applied to the pacer control circuit 22.

Referring further to FIG. 3, the pacer control circuit 22 is seen to include a pacing and threshold determination control circuit 51 which controls both the generation of the pacing pulse pairs and the determination of the patient's capture threshold. Various characteristics of the generated pacing pulses, including pulse amplitude, pulse duration and pulse spacing, are determined in accordance with control inputs developed by pacer control circuit 22 and applied to pacing pulse generator 23.

Capture threshold is automatically determined in accordance with the system and method described in the present inventor's copending application Serial No. 738,609, filed May 28, 1987 entitled "Automatic Cardiac Capture Threshold Determination System." In determining a patient's capture threshold, the pacer control circuit 22, pacing pulse generator 23 and capture detect circuit 27 function to incrementally vary the energy of applied pacing pulses, while simultaneously monitoring the response of the heart, in order to identify the minimum pacing pulse energy required to reliably stimulate contractions in the heart.

To develop the digitally encoded instructions for setting the energy of the pacing pulses, the pacer control circuit 22 includes a pair of data registers 52 and 53 which store a pair of variables $X_L$ and $X_H$ respectively. Variable $X_L$ represents a low pulse-energy level which is insufficient to induce cardiac contraction, while variable $X_H$ represents an energy level which is sufficiently high to reliably stimulate contractions of the heart. The system further includes a digital averaging circuit 54 for computing the arithmetic average of the $X_L$ and $X_H$ variables, as well as an additional register 55 for storing the arithmetic average so computed. A digital comparator 56, coupled to the outputs of registers 52 and 53, is also provided for comparing the $X_L$ and $X_H$ variables.

As further illustrated, the system includes a read only memory (ROM) 57 having five memory locations 58–62 in which five constants, $C_1$–$C_5$, are stored. Each of the constants can be retrieved from ROM 57 under the direction of the pacing and threshold determination control circuit 51, which also controls the input and output of data from registers 52, 53 and 55.

The outputs of registers 53 and 55, as well as the output of ROM space 61, are coupled through a three input data switch 62 to the input of a pulse level register 63. The output of register 63 is coupled through a two-position data switch 64 to the pacing pulse generator 23.

The energy of the generated pacing pulses is determined by the value stored in the pulse level register 63. The source of the pulse level variable stored in register 63 can be either register 53, register 55 or ROM space 61, and is determined by the position of data switch 62 under the control of the pacing and threshold determination control circuit 51.

Figure 4:
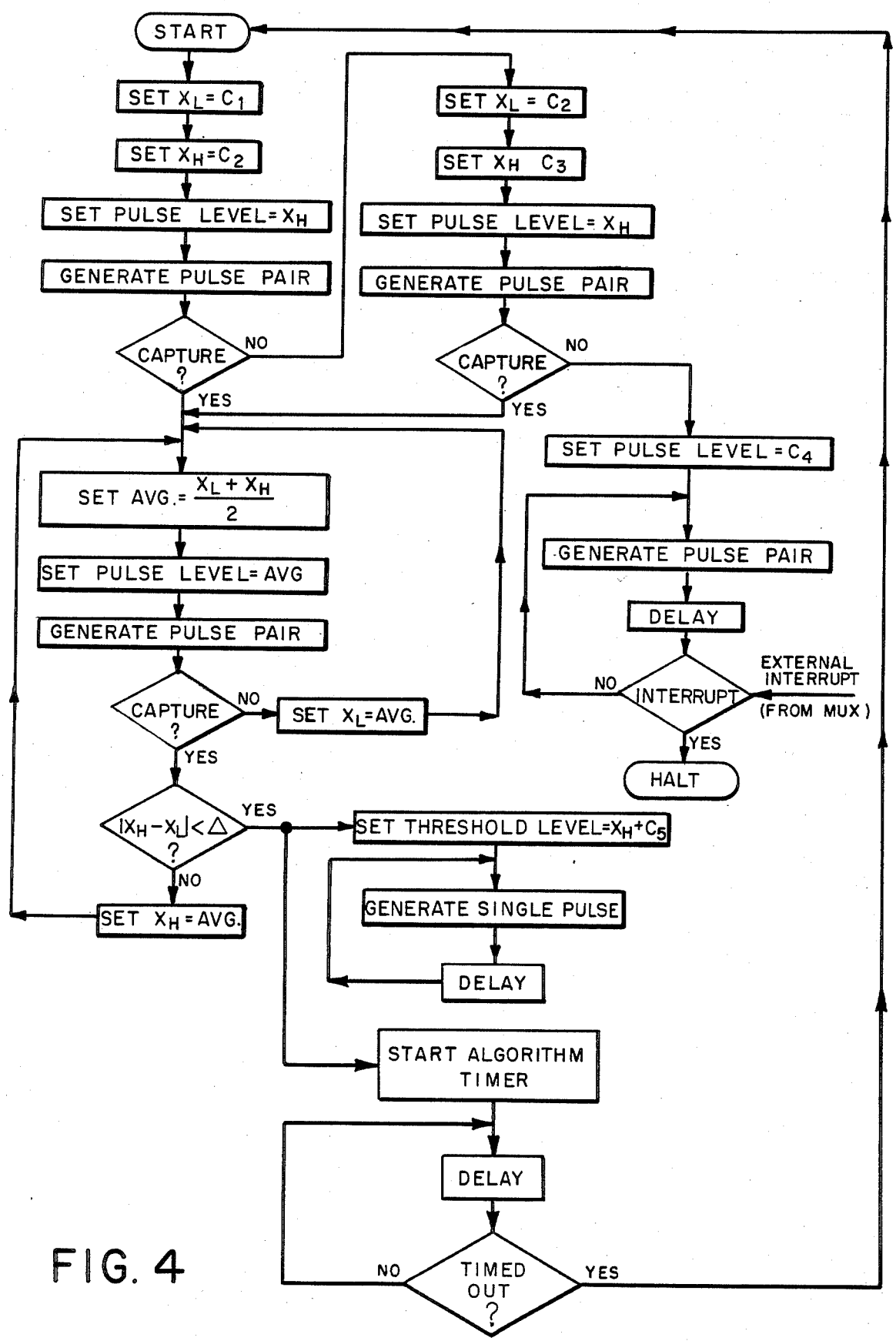
FIG. 4 is a logic flow diagram useful in understanding the operation of the system illustrated in FIG. 3.

The operation of the pacer can be understood by reference to the block diagram of FIG. 3 and the logic flow diagram of FIG. 4. Upon receipt of a start command, the threshold determination control circuit 51 causes predetermined constant $C_1$ to be loaded into $X_L$ register 52 and constant $C_2$ is loaded into $X_H$ register 53. $C_1$ represents a pacing energy level at which cardiac capture is statistically unlikely to occur and for convenience may be set equal to zero. Constant $C_2$ represents a pulse energy level at which capture is statistically likely to occur and is preferably empirically derived.

Following such initialization of the $X_L$ and $X_H$ variables, the content of register 53 is coupled through data switch 62 into the pulse level register 63 and from there to pulse generator 23. Accordingly, the initial pulse level will correspond to that of constant $C_2$. A pulse pair at the $C_2$ energy level is then generated after which capture detect circuit 27 determines whether an induced cardiac contraction has occurred.

In the event capture does not occur at the $C_2$ pulse energy level, constant $C_2$ is loaded into the $X_L$ register 52 while constant $C_3$, in ROM space 60, is loaded into the $X_H$ register 53. The updated content of register 53 is then loaded into the pulse level register 63 with the result that pulse generator 23 is set to a new energy level corresponding to constant $C_3$. Constant $C_3$ represents a greater energy level than constant $C_2$ and has been statistically determined to be even more likely to result in capture. Thereafter, a pulse pair at the $C_3$ level is generated and the response of the heart noted.

In the event capture does not occur at the energy level corresponding to constant $C_3$, the pacer automatically reverts to operation in a basic life support, or "STAT" mode, in which pacing pulses are developed at an energy level which has been experimentally determined to virtually assure capture. This level, represented by constant $C_4$, is developed by loading the content of ROM space 61 into the pulse level register 63. After each pulse pair at the $C_4$ energy level is generated, a check is made to determine whether an external interrupt signal from multiplexer 28 (FIG. 2) has been received. If not, the pulse generator once again develops a pulse pair for application to the heart. The delay is such that the heart will be paced at a rate consistent with basic life support in order to assure the safety of the patient. Operation in this mode will continue in the absence of any external intervention.

In the event pulses at either the $C_2$ or $C_3$ energy levels did result in capture the pacing pulse level is systematically decreased until a pulse energy, insufficient to cause cardiac capture, is reached. This is accomplished by loading the contents of $X_L$ and $X_H$ registers 52 and 53 into the averaging circuit 54 to define a third variable "AVG" corresponding to the arithmetic average of the then existing $X_L$ and $X_H$ values. The AVG value is then loaded into AVG register 55 and from there, through data switch 62, into pulse level register 63. Next a pulse pair at the AVG level is generated and the response of the heart noted.

In the event capture is not detected, control circuit 51 causes the content of AVG register 55 to be loaded into $X_L$ register 52 with the result that variable $X_L$ is increased to the currently existing AVG level. A new average, using the updated value of $X_L$, is then computed and loaded into AVG register 55 after which a pulse pair at the new AVG energy level is generated. In the event capture is still not detected, $X_L$ is once again updated to the current AVG value, after which the average is once again recalculated. This process continues until capture is detected.

In the event the AVG energy level is sufficient to cause cardiac capture, pacing pulse energy will be reduced until capture no longer occurs. This is accomplished by loading the content of AVG register 55 into $X_H$ register 53 in order to update variable $X_H$ to the then existing value of variable AVG. The new average is then recomputed using the new $X_H$ value and the result loaded into AVG register 55. A pulse at the new AVG energy level is generated and the response of the heart noted. In the event capture still occurs, the pulse energy level is once again reduced in the same iterative manner.

Prior to setting $X_H$ equal to AVG, digital comparator 56 determines the difference between the respective values of $X_H$ and $X_L$. If $X_H$ and $X_L$ differ by less than a predetermined amount, it can be assumed that variable AVG will be substantially equal to the actual capture threshold. For safety and reliability however, variable $X_H$ is preferably selected as the capture threshold level. Accordingly, when $X_H$ and $X_L$ are found to differ by less than the predetermined value, digital comparator 56 returns a "TEST COMPLETE" control signal to control circuit 51. Preferably, this occurs when the difference between $X_H$ and $X_L$ equals the minimum incremental pulse level change (i.e., resolution) available from pacing pulse generator 23.

It will be observed that in general variable $X_H$ represents the minimum pulse energy at which capture has at some point actually been detected, while variable $X_L$ represents the maximum pulse energy at which capture has not yet been detected. It will be apparent that as the system operates, the numerical value of $X_H$ will progressively decrease, while the value of variable $X_L$ will progressively increase. Thus, the operation is such that $X_L$ and $X_H$ will at all times bracket the actual capture threshold. $X_H$ and $X_L$ continue converging in this manner until digital comparator 56 determines that the variables differ by less than the predetermined difference value.

Once determined, the patient's capture threshold can be used in setting the energy of the generated pacing pulses. The precise relation between capture threshold and the pacing energy level is chosen in accordance with the application in which the pacer is to be used. For example, it may be desirable to pace the heart at some constant increment above or ratio to the capture threshold energy level. For example, with constant current pacing, it may be desirable to operate at 1.5 times the capture threshold, or 0.5mA above it, whichever is greater. When it is desired to minimize battery current drain, operation slightly above the capture threshold energy level is preferable. To this end, the pacer control circuit 22 further includes a digital adder 65 coupled to ROM space 62 and, through data switch 64, to the output of pulse level register 63. Once the capture threshold has been determined, the content of pulse level register 63, as well as constant $C_5$ in ROM space 62, are loaded into adder 65 with the effect that the pacing pulse energy level corresonds to the capture threshold level incremented by constant $C_5$. Constant $C_5$ thereby serves as a "safety margin" and assures pacing reliability when the pacer is operated near the actual capture threshold. The value of $C_5$ is not critical and depends primarily on the degree of pacing reliability required.

Once the pacing energy level has been set in accordance with the capture threshold, it will be appreciated that, since the energy level of the generated pacing pulses has been increased by constant $C_5$, the first pulse of each pulse pair will be the pulse which causes capture. Thus, the second pulse of each pair becomes redundant. Therefore, to further reduce battery drain, the second pulse of the pair can be eliminated without affecting pacing reliability as long as the energy of the first pulse remains slightly above the actual capture threshold.

To provide for operation in a single pulse mode, the pacer includes a mode select circuit 66 which selects whether pacing pulse generator 23 develops single or paired pacing pulses in response to each pulse generation control signal from pacing and threshold determination control circuit 51. When control circuit 51 receives the "TEST COMPLETE" control voltage indicating that capture threshold has been determined and that the pulse level has been set in accordance therewith, a similar control voltage is applied to mode select circuit 66. Upon receiving this control voltage, mode select circuit 66 conditions pulse generator 23 to begin producing single pacing pulses while at the same time inhibiting further operation of the automatic capture threshold determination system.

Since capture threshold can vary over time, it is necessary to assure that the pacing pulse level remains sufficient to reliably stimulate capture. Accordingly, mode select circuit 66 operates to periodically allow the redetermination of the capture threshold and the setting of pulse level in accordance therewith. To this end, after the passage of a suitable time period (e.g., 12 hours), the mode select circuit 66 enables the capture threshold determination circuitry and once again provides for generation of pacing pulse pairs. Once capture threshold has been redetermined and pacing level reset, the pacer once again reverts to operation in a single pulse mode.

Since it is possible for the capture detect circuit 27 to generate a "capture detected" signal in the event a naturally occurring cardiac contraction occurs during the application of a pulse pair to the heart, a false capture indication could, conceivably, be made. To prevent system response to such false capture indications, the pacing and threshold determination control circuit 51 can be arranged to require the occurrence of a number of detected cardiac contractions, in response to a like number of consecutive applied pacing pulse pairs, before the existence of a capture condition is accepted. For example, since it is extremely improbable that three consecutive naturally occurring contractions will occur in synchrony with three applied pacing pulses, the production of three consecutive capture detected signals from capture detect circuit 27 provides a highly reliable indication that the cardiac contractions are occurring in response to the applied pacing pulses. Accordingly, the pacing control circuit 51 preferably requires the occurrence of three consecutive induced contractions before the existence of a capture condition is accepted. This criterion need be applied only in the vicinity of threshold.

The incorporation of an automatic capture threshold determination system into a cardiac pacer permits pacer operation in a number of previously unavailable operating modes. The system as described herein is well suited for use in both external and implantable pacers and greatly reduces the need for post-implantation manual alteration of the pacer operating parameters.

It will be appreciated that while discrete system components, such as the various registers, comparators, and control circuits have been shown and described, the system may be advantageously implemented using microprocessor-based circuitry in conjunction with appropriate programming. Additionally, it will be appreciated that variation of the pacing energy level can be accomplished through variation of either, or both, of the pacing pulse amplitude and the pulse duration. Furthermore, it will be appreciated that while various constants have been identified and described, these constants can be adjusted to suit the particular needs of individual patients without departing from the scope of the invention.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A cardiac pacer for stimulating contractions in a patient heart having a recurring refractory period of predetermined minimum duration, comprising:
    means for establishing a pacing period within the refractory period of the heart;
    pacing pulse generating means for generating a series of pacing signals for application to the heart, said generating means having a first operating mode wherein each of said pacing signals comprises a single pulse occurring during said refractory period, and a second operating mode wherein each of said signals comprises a pair of pulses occuring during said pacing period, the energy level of said pulses in said first operating mode being dependent on an applied amplitude control signal;
    means defining recurring test periods;
    pacer control means for conditioning said pacing pulse generating means to said second operating mode during each of said test periods;
    capture thereshold detection means responsive to contractions within the heart induced by paired pulses from said generating means during said second mode of operation thereof, periodically operable during each of said recurring test periods for automatically determining the minimum pacing pulse energy required during each of said test periods to reliably stimulate contractions in the patient heart; and
    amplitude control means responsive to said capture threshold detection means for providing following each of said test periods an amplitude control signal to said pacing pulse generating means to cause said generating means to thereafter generate pacing pulses having an energy level related to said capture threshold.

2. A cardiac pacer as defined in claim 1 wherein said amplitude control signal developed by said amplitude control means exceeds said threshold level by a predetermined margin factor whereby the energy level of said pacing pulses set by said amplitude control means exceeds said capture threshold by said margin factor.

3. A cardiac pacer for stimulating contractions in a patient heart having a recurring refractory period of predetermined minimum duration, comprising:
   pacing pulse generating means for generating recurring pacing signals for application to the heart, said pacing means having a first operating mode wherein each signal comprises a single pulse, and a second operating mode wherein each signal comprises a pair of closely spaced pulses;
   means defining recurring test periods;
   pacer control means for conditioning said pacing pulse generating means to said second operating mode during said recurring test periods;
   capture threshold detection means responsive to contractions of the heart in response to said closely spaced pulses during each of said test periods for determining the capture threshold of the heart; and
   amplitude control means for causing said generating means to generate pacing pulses at an energy level related to said determined capture threshold during said first mode of operation.

4. A caridac pacer as defined in claim 3 wherein said amplitude control signal developed by said amplitude control means exceeds said threshold level by a predetermined margin factor whereby the energy level of said pacing pulses set by said amplitude control means exceeds said capture threshold by said margin factor.

5. A cardiac pacer as defined in claim 3 wherein said pacer includes means for establishing a pacing period within the refractor period of the heart, and said closely spaced pair of pulses generated by said generating means occur during said pacing period.

6. A cardiac pacer as defined in claims 1 or 5 wherein said closely spaced pulses are generated with equal amplitudes, and said capture thereshold detection means compare said generated closely-spaced pacing pulses with the electrical response of the heart thereto during said test period to detect capture at the energy level of said pulses.

7. A cardiac pacer as defined in claim 6 wherein capture threshold determination means vary energy level of said generated closely spaced pulses within a range extending above and below said capture threshold.

8. A power-conservative method of pacing a patient heart comprising the steps of:
   defining first and second operating modes;
   generating recurring pacing signals for application to the heart wherein, said pacing signals each comprising a single pacing pulse in said first mode of operation, and a pair of closely spaced pulses in said second mode of operation;
   periodically analyzing contractions to the heart resulting from the closely spaced double pacing pulses in said second mode to determine the capture threshold of the heart; and
   maintaining the amplitude of said pacing pulses at an amplitude related to said capture threshold during said first mode of operation.

9. A method of pacing as defined in claim 8 comprising the additional step of maintaining the amplitude of said pacing pulses above that of said capture threshold by a predetermined margin factor.

10. A method of pacing as defined in claim 8 including the additional step of establishing a pacing period within the refractory period of the heart, and wherein said generating of recurring pacing signals comprises generating said closely spaced pulses during said pacing period.

11. A method of pacing as defined in claim 10 wherein said generating means generate said closely spaced pulses at equal amplitudes, and including the additional step of comparing said generated closely spaced pulses with the electrical response of the heart thereto to detect capture at the energy level of said pulses.

12. A method of pacing as defined in claim 11 includes the additional step of varying the energy level of said generated closely spaced pulses within a range extending above and below said threshold level.

* * * * *